United States Patent [19]

Bye

[11] Patent Number: 4,575,954

[45] Date of Patent: Mar. 18, 1986

[54] SHOE CONSTRUCTION WITH FOOT AND ANKLE RESTRAINING MEANS

[76] Inventor: Michael E. Bye, 13910 SE. Aldridge Rd., Portland, Oreg. 97236

[21] Appl. No.: 580,937

[22] Filed: Feb. 16, 1984

[51] Int. Cl.⁴ .............................................. A43B 7/20
[52] U.S. Cl. ........................................ 36/89; 36/114; 36/58.5; 36/10; 2/DIG. 6; 2/240
[58] Field of Search ................ 36/88, 89, 99, 83, 58.5, 36/58.6, 1, 11.5, 9 R, 70; 2/239, 240, DIG. 6

[56] References Cited

U.S. PATENT DOCUMENTS

| | | | |
|---|---|---|---|
| 527,717 | 10/1894 | Pendergast | 36/9 R |
| 1,499,167 | 6/1924 | Frisch | 36/58.5 X |
| 2,238,804 | 4/1941 | Brown | 36/10 |
| 2,422,410 | 6/1947 | Gross | 36/10 |
| 2,830,585 | 4/1958 | Weiss | 128/166 |
| 3,059,350 | 10/1962 | Price | 36/11.5 |
| 3,122,906 | 3/1964 | Crawford | 2/240 X |
| 3,613,273 | 10/1971 | Marquis | 36/89 |
| 3,674,023 | 7/1972 | Mann | 128/166 |
| 3,834,377 | 9/1974 | Lebold | 128/80 H |
| 3,938,264 | 2/1976 | Burrell | 36/1 |
| 3,970,083 | 7/1976 | Carrigan | 128/166 |
| 3,983,870 | 10/1976 | Herbert et al. | 2/240 X |
| 4,187,619 | 2/1980 | Gibbs | 36/10 |

FOREIGN PATENT DOCUMENTS

| | | | |
|---|---|---|---|
| 494979 | 8/1953 | Canada | 36/89 |
| 3111227 | 9/1982 | Fed. Rep. of Germany | 36/58.5 |

*Primary Examiner*—Werner H. Schroeder
*Assistant Examiner*—T. Graveline
*Attorney, Agent, or Firm*—James D. Givnan, Jr.

[57] ABSTRACT

A shoe having an upper the interior of which is provided with closure material. Cooperating closure material is in place on the exterior of a foot covering and adheres to the shoe upper mounted material to join the foot covering and shoe upper in a positive, non-slip manner. Adhesive material on the interior of the foot covering adheres to the skin of the foot and ankle. Extreme lateral displacement of the foot in an inward or outward direction is restrained by the shoe upper being put in tension. Upright stays prevent sagging of the shoe upper.

4 Claims, 7 Drawing Figures

U.S. Patent     Mar. 18, 1986     4,575,954
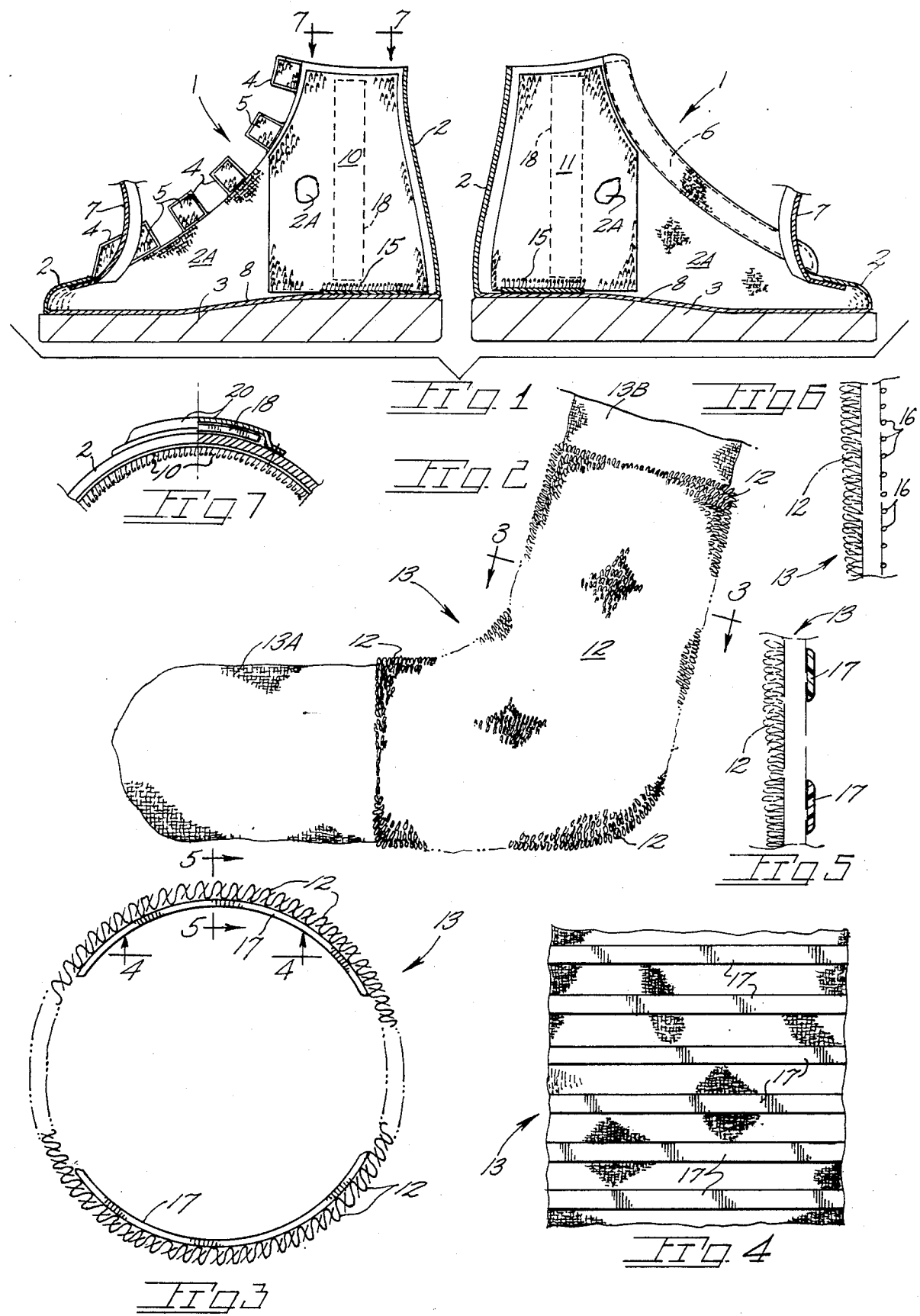

SHOE CONSTRUCTION WITH FOOT AND ANKLE RESTRAINING MEANS

BACKGROUND OF THE INVENTION

The present invention pertains generally to footwear of the type used in athletics and particularly to footwear intended to prevent ankle sprains.

A common injury to athletes, as well as those engaging in recreational athletics, is the ankle sprain. Excessive inward lateral displacement of the foot often stretches ligaments of the ankle increasing the probability of recurring ankle sprains. To alleviate this problem, athletes commonly wear elastic stocking and/or wrap the weakened ankle with tape. Such taping of ankles is time consuming, costly and provides only a partial safeguard against later sprains. Similarly, the use of various elastic foot coverings or bands is of limited value.

Regardless of whatever safeguards are employed against extreme lateral displacement, the foot must remain capable of normal flexion to the extent participation in athletics is not hampered.

Devices to provide ankle and foot support, usually for orthopedic purposes, have included tight knit elastic ankle bands, air bladders, laced up fabric ankle braces, stretch fabric banding and ordinary cloth tape, to namel a few and some of which are disclosed in U.S. Pat. Nos. 3,674,023; 3,970,083; 4,280,489; 4,367,733; 3,834,377; 4,166,460; 2,830,585.

SUMMARY OF THE PRESENT INVENTION

The present invention is embodied in footwear construction which inhibits inward lateral rolling of the ankle without unduly restricting foot flexion about the ankle joint in fore and aft directions.

The present shoe construction includes the provision of means on the shoe interior which cooperates with a foot covering to prevent inward turning or rolling of the foot beyond a non-injurious point. Loads encountered in resisting such movement are ultimately bourne by the shoe upper. The foot covering is in frictional contact with the epidermis of the foot and ankle area of the lower leg. Use is made of a fabric closure material carried by the shoe upper and the foot covering in one form of the invention. Accordingly, the foot is restrained against extreme lateral displacement without hindrance of normal fore and aft flexion. Further, the present arrangement is not unduly cumbersome to wear or apply to the foot.

Important objects include the provision of footwear and a foot covering which cooperates to prevent inward or outward lateral displacement of the foot beyond the normal range of travel; the provision of footwear which has a non-stretch shoe upper which is in tension during lateral rolling displacement of the foot; the provision of a shoe upper and a foot covering which include cooperating adhering members; the provision of ankle supporting footwear not unduly cumbersome to put on or wear and which avoids the costly use of tape; the provision of a shoe and foot covering for wear by those having chronic foot ailments.

BRIEF DESCRIPTION OF THE DRAWINGS

In the drawings:

FIG. 1 is a vertical sectional view taken lengthwise along a piece of footwear made in accordance with the present invention;

FIG. 2 is a fragmentary side elevational view of a foot covering made in accordance with the present invention;

FIG. 3 is a horizontal sectional view taken downwardly along line 3—3 of FIG. 2;

FIG. 4 is a vertical elevational view of the footwear taken along line 4—4 of FIG. 3;

FIG. 5 is a vertical sectional view of the footwear taken along lines 5—5 of FIG. 3;

FIG. 6 is a view similar to FIG. 5 but showing modified footcovering construction, and FIG. 7 is a fragmentary plan view of the footwear upper taken along line 7—7 of FIG. 1.

DETAILED DESCRIPTION OF THE PREFERRED EMBODIMENTS

With continuing attention to the drawing wherein applied reference numerals indicate parts hereinafter similarly identified, the reference numeral 1 indicates generally a high top athletic shoe having an upper 2 of flexible, non-stretch construction. A sole structure at 3 is intended to be typical and may take various forms depending on shoe use.

For securement on a foot in a snug manner, the shoe upper preferably may include several tabs as at 4 each provided with a fabric closure piece 5 which adheres to a cooperating fabric closure strip 6 in place on the exterior of the shoe upper.

Obviously, other types of shoe securement means may be utilized such as conventional shoe laces without adversely affecting use of the later described novel combination of the present invention. A shoe tongue is at 7.

Affixed by suitable means to the interior surface at 2A of the upper are expanses of fabric closure material 10–11 extending from proximate a shoe insole 8 to the top edge. The closure material pieces 10–11 are preferably of the "hook" material of that type of closure material sold under the registered trademark VELCRO. A modified shoe upper may utilize like areas of closure material in the form of sticky surface material such as that known as "sticky" back tape.

Additional closure material at 12 is of a looped nature in place on a sock-like, one way elastic foot covering generally at 13 and cooperates with earlier mentioned closure material 10 and 11 and is preferably integral with the foot covering as by being woven into the foot covering at the time of manufacture. Material 12 may be a portion of a sock having toe and loewr leg covering areas as at 13A–13B which may be free of closure material. Accordingly, upon wearing of foot covering 13 the closure material pieces 10–11 and material 12 come into mating, adhering engagement with one another to effect securement of the foot covering with respect to the interior of the shoe upper. The additional closure material 12 is of looped pile to provide adherence to the hook shaped material at 10 and 11 on the shoe upper.

If so desired, pieces of closure material at 15 may be of hook shape and affixed in place on the heel segment of shoe insole 8 by suitable means, such as an adhesive. Slippage of the foot with respect to the shoe insole is thereby inhibited to prevent undesired lost motion between foot and shoe.

The foot covering in FIGS. 2 and 3 is shown as being of woven tubular construction with closure material 12 woven into same and extending thereabout. While such may contribute to ease of manufacture, the foot covering may be otherwise embodied as for example in an athletic stocking or ankle band having a looped filament outer surface which may stretch in a radial direction about the foot but is virtually non-elastic in a lengthwise or axial direction of the band.

Frictional adherence of the foot covering to the epidermis of the ankle area is preferably accomplished by adhesive means on the interior of the foot covering. With reference to FIGS. 4 and 5 the interior surface of the foot covering may be provided with a surfacial adhesive 17 such as a soft vinyl. Alternately, as shown in FIG. 6, the foot covering may be incorporated into the footwear in the form of rubber filaments 16 extending about the interior of the foot covering and located so as to come into adhesive contact with the skin of the ankle and foot. The area of the adhesive surface or filament would approximate the location of external area 12 of the closure material. A still further alternative is the use of a double sided or "sticky back" adhesive tape wrapped about the skin of the foot and ankle.

The shoe upper 2 may be provided with stays at 18 each in upright placement along opposite sides of the upper and retained in place as by a cover strip 20. The stays serve to retain the sides of the upper against sagging and may be embodied in strips of metal or synthetic material which may distort along their respective axes during fore and aft flexion of the ankle joint.

The surface adhesive material 17 applied to the interior of the foot covering may be a soft polyvinylchloride applied in a pattern as by spraying through a mask to assure the foot covering has adequate absorptive qualities.

The use of the present invention in combination with a "low cut" shoe (not shown) provides a system for securing a foot within an athletic shoe to avoid undesired lost motion between foot and shoe during starting and stopping maneuvers.

In certain instances it may be desirable to dispense with the adhesive means from the interior of the foot covering and instead rely on frictional engagement of the foot covering material which, as earlier noted, may include an elastic band which is in gripping engagement with the epidermis of the ankle and foot.

While I have shown but a few embodiments of the invention it will be apparent to those skilled in the art that the invention may be embodied still otherwise without departing from the spirit and scope of the invention.

Having thus described the invention, what is desired to be secured under a Letters Patent is:

I claim:

1. In combination,
   high-top athletic footwear having an upper and an insole,
   a foot covering of fabric construction including interior adhesive means for adhering contact with the epidermis of the wearer's foot, and
   an expanse of closure material carried interiorly by the footwear upper and extending substantially between the shoe insole and the top edge of the upper, additional closure material carried by the exterior of the foot covering and engageable with said expanse of closure material to prevent slippage between the upper and the foot covering whereby extreme lateral rolling movement of the foot is inhibited by the footwear by reason of the upper thereof being put into tension.

2. The combination claimed in claim 1 wherein said expanse of closure material is an expanse of adhesive material fixed interiorly in place on the shoe upper.

3. The combination claimed in claim 1 wherein said additional closure material has an outer surface of looped construction.

4. The combination claimed in claim 1 wherein said adhesive means are resilient bands of material.

* * * * *